US00PP34080P2

(12) United States Plant Patent
Villegas

(10) Patent No.: US PP34,080 P2
(45) Date of Patent: Mar. 29, 2022

(54) ***SANSEVIERIA* PLANT NAMED 'GRAELYN'**

(50) Latin Name: *Sansevieria aubrytiana*
Varietal Denomination: Graelyn

(71) Applicant: FLORICA FARMS, INC., Eustis, FL (US)

(72) Inventor: Marvin Gonzalez Villegas, Alajuela (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 17/521,755

(22) Filed: Nov. 8, 2021

(51) Int. Cl.
*A01H 6/12* (2018.01)
*A01H 5/00* (2018.01)

(52) U.S. Cl.
USPC ..... Plt./382

(58) Field of Classification Search
USPC ..... Plt./382
See application file for complete search history.

*Primary Examiner* — Annette H Para
(74) *Attorney, Agent, or Firm* — Foley & Lardner LLP

(57) ABSTRACT

A new and distinct cultivar of *Sansevieria aubrytiana* plant named 'Graelyn' particularly characterized by its variegated foliage with different green tones on the irregular bands and light green colored irregular bands in the backside of the leaf blade; wide and lanceolate leaves, supported in a rosette; 60-90 cm plant height; erect plant habit, high drought tolerance with low need for water and resistant to antrachnose (*Colletotrichum sansevieriae*) disease.

3 Drawing Sheets

Figure 1:
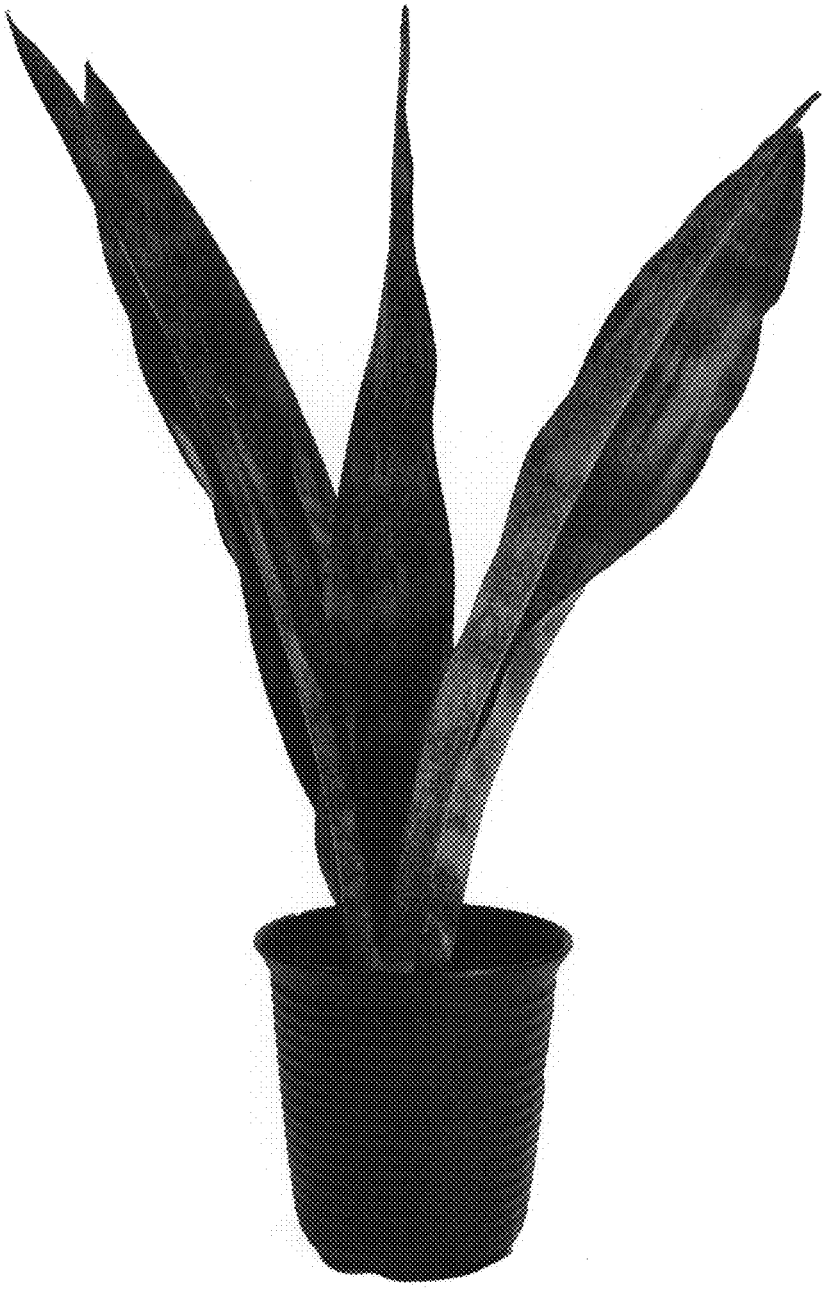

Latin name of the genus and species of the claimed plant: *Sansevieria aubrytiana.*

Variety denomination: 'GRAELYN'.

BACKGROUND OF THE INVENTION

The present invention relates to a new and distinct cultivar of *Sansevieria* plant, botanically known as *Sansevieria aubrytiana*, of the family Asparagaceae, hereinafter referred to by the cultivar name 'Graelyn'.

*Sansevieria* is a monocotyledonous flowering plant which can be produced in either hard-leafed or soft-leafed varieties for interior use as a house plant or outdoors ornamental plant.

The new *Sansevieria* 'Graelyn', originated from a naturally-occurring mutation of the *Sansevieria* 'Sayuri' (unpatented). The new *Sansevieria* 'Graelyn' was discovered and selected by the inventor, Marvin Gonzalez Villegas, as a single sprouting rare mutation in a controlled environment in Monterrey, San Carlos, Alajuela Province, Costa Rica.

Asexual reproduction of the new *Sansevieria* cultivar by vegetative cuttings was first performed in July 2016 in Monterrey, San Carlos, Alajuela Province, Costa Rica, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Graelyn', which in combination distinguish this *Sansevieria* as a new and distinct cultivar:

1. Variegated foliage with different green tones on the irregular bands and light green colored irregular bands in the backside of the leaf blade.
2. Wide and lanceolate leaves, 60-80 cm and supported in a rosette.

3. 60-90 cm plant height.
4. Plant habit: Erect.
5. Needs little water and is very drought tolerant.

The new variety 'Graelyn' presents an average of 6-8 leaves per plant when it reaches its maturity (between 6-10 months). The new variety has an erect growth habit, and the entire plant can reach a height between 60-90 cm. The leaves are slightly wide (7-10 cm average measured at the widest part of the mature leaf) and lanceolate with a soft waxy texture. The plant has a cylindrical shape.

The new variety is moderately drought tolerant, adapts to conditions of light and shade, and shows resistance to antrachnose (*Colletotrichum sansevieriae*) disease.

Plants of the new *Sansevieria* 'Graelyn' differ from plants of the parental cultivar 'Sayuri' (unpatented) in the characteristics described in Table 1.

TABLE 1

Comparison with Parental Varieties

| Characteristic | New Cultivar 'Graelyn' | Parent 'Sayuri' (unpatented) |
|---|---|---|
| Plant Vigor | Similar vigor. | Similar vigor. |
| Color | Variegated foliage with different green tones on the irregular bands and light green colored irregular bands in the backside of the leaf blade. | Variegated leaves (different green tones on the irregular bands). |
| Shape | Wide and lanceolate leaves in a rosette. | Wide and lanceolate leaves in a rosette. |
| Texture of leaves | Smooth-textured leaves. | Smooth-textured leaves. |

Of the many commercial cultivars known to the present inventor, the most similar in comparison to the new *Sansevieria* 'Graelyn' is the *Sansevieria* 'Black Coral' (unpatented) in the characteristics described in Table 2:

TABLE 2

| Comparison with Comparison Cultivar | | |
|---|---|---|
| Characteristic | New Cultivar 'Graelyn' | Comparison Cultivar 'Black Coral' (unpatented) |
| Plant Vigor | More vigorous. | Less Vigorous. |
| Color | Variegated foliage with different green tones on the irregular bands and light green colored irregular bands in the backside of the leaf blade. | Variegated leaves (different variegated leaves green tones on the irregular (different green bands) and light green colored tones on the stripes along the margins irregular bands). |
| Shape | Wide and lanceolate leaves in a rosette. | Wide and lanceolate leaves in a rosette. |
| Texture of leaves | Smooth-textured leaves. | Smooth-textured leaves. |

BRIEF DESCRIPTION OF THE PHOTOGRAPHS

The accompanying photographs illustrate the overall appearance of the new *Sansevieria* cultivar 'Graelyn' showing the colors as true as is reasonably possible with colored reproductions of this type. Colors in the photographs may differ slightly from the color value cited in the detailed botanical description which accurately describe the color of 'Graelyn'.

FIG. 1—Shows a side view of a six-month old plant of *Sansevieria* 'Graelyn' in a 26 cm diameter pot.

Figure 2:
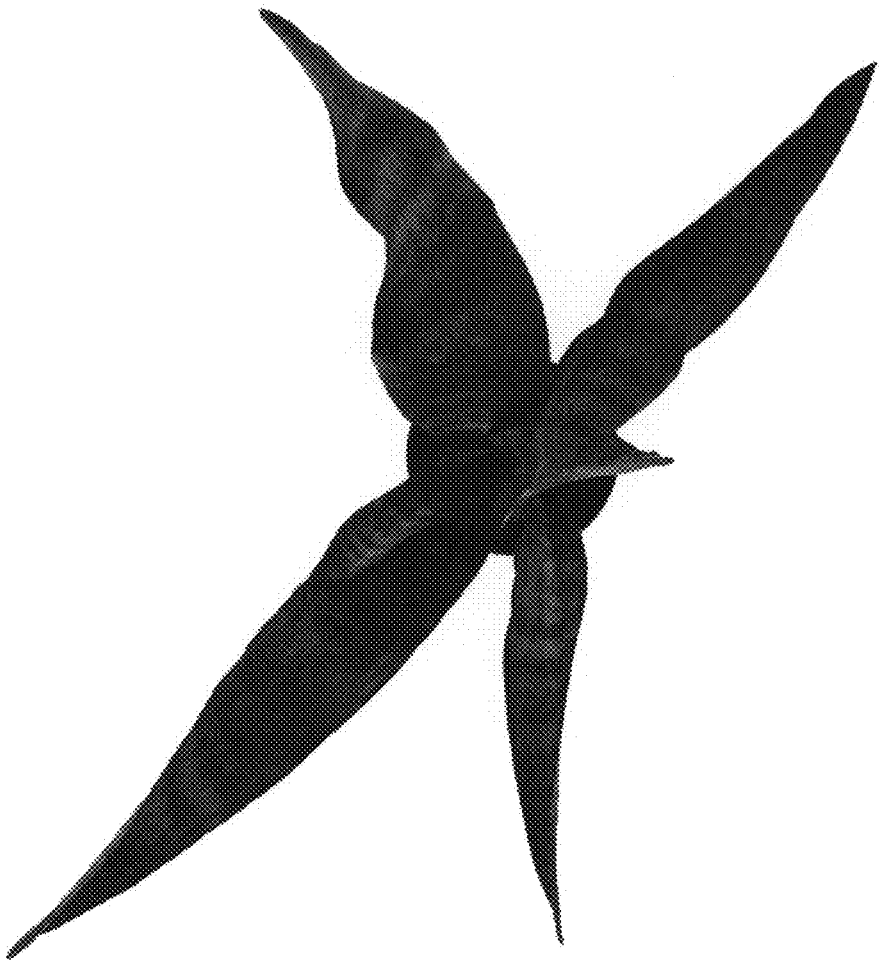

FIG. 2—Shows a pot down view of a typical six-month-old plant of *Sansevieria* 'Graelyn'.

Figure 3A:
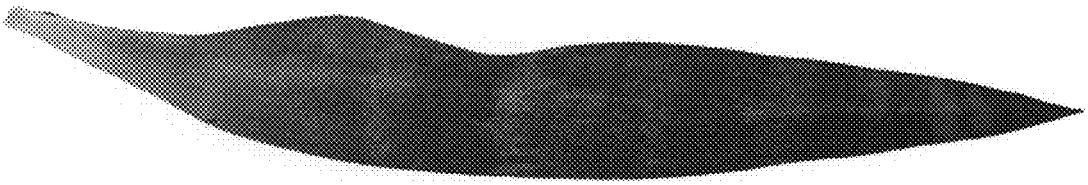
Figure 3B:
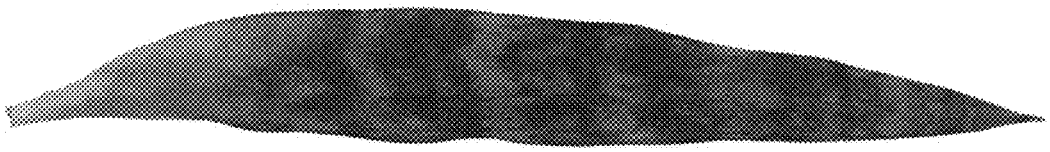

FIGS. 3A-3B—Shows a close-up view of the typical leaves of *Sansevieria* 'Graelyn' from a six-month old plant (upper side—A, under side—B).

DETAILED BOTANICAL DESCRIPTION

The new *Sansevieria* 'Graelyn' has not been observed under all possible environmental conditions. The phenotype of the new cultivar may vary with variations in environment such as temperature, light intensity, and day length without any change in the genotype of the plant.

The photographs, together with the following observations, measurements and values describe the new *Sansevieria* cultivar 'Graelyn' as grown in open field conditions in Monterrey, San Carlos, Alajuela province, Costa Rica, which closely approximate those generally used in commercial practice. 'Graelyn' was grown in tropical lowlands in Costa Rica with day lengths of 12 to 13 hours and ambient temperature to 85 degrees. The level of relative humidity was 80%. No supplementary artificial light is necessary.

This crop does not require constant fertilization, to increase production per area about 200 kg ha−1 N, 150 kg ha−1 of P and 100 kg-ha K are required, the production is closely related with soil conditions in which they are grown.

Color references are made to The Royal Horticultural Society Color Chart (R.H.S.), except where general colors of ordinary significance are used. The photographs and descriptions were taken where general colors of ordinary significances are used. The photographs and descriptions were taken during the rainy season in Monterrey, San Carlos, Alajuela province, Costa Rica, with outdoor day temperatures of 24.5° C. during the day and 18° C. at night. The age of the plants described is 8 months.

Classification:

*Botanical.*—*Sansevieria aubryitiana.*

*Variety denomination.*—'Graelyn'.

Parentage: *Sansevieria aubryitiana* 'Sayuri' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to a low temperature of about 12° C. and tolerant to a high temperature of about 35° C.

*Fertilization.*—200, 150 and 100 kg $ha^{-1}$ of N, P and K.

*Growth regulators.*—Not necessary.

Propagation:

*Type.*—Vegetative, by rooted cuttings.

*Rooting habit and description.*—Rhizomes, with short roots.

*Time to initiate roots.*—About 12 to 22 days at 20-25° C.

*Time to produce a rooted cutting.*—About 15 to 22 days at 20-22° C.

Plant:

*General appearance and form.*—

*Height.*—About 90 cm when grown in ground. about 60 cm when grown in a 26 cm size container.

*Spread.*—About 15 cm when grown in ground. About 12 cm when grown in 26 cm size container.

*Form.*—Monocot; leaf bases arranged in a rosette around growth point.

*Shape.*—Cylindrical.

*Growth rate and habit.*—About 2 cm per week; upright.

*Fragrance.*—None.

*Stem.*—Modified (Rhizome and foliage). Length: About 12 cm when grown in ground. About 8 cm when grown in 21 cm size container. Diameter: About 3.0 cm to 4.0 cm. Shape: Round. Texture: Rough. Color: RHS 4D. Strength: Strong and durable. Internode length: About 0.6 mm to 0.8 mm.

Foliage:

*Quantity.*—About 4-6 leaves.

*Arrangement and attachment.*—Single, alternate; leaf bases arranged in a rosette around growth point.

*Leaf length.*—About 30 cm.

*Leaf width.*—About 9 cm.

*Overall shape of leaf.*—Lanceolate.

*Apex shape.*—Acute, triangular.

*Base shape.*—Plane.

*Margin.*—Sharp, smooth.

*Texture.*—Upper Surface: Smooth and waxy texture. Under Surface: Smooth and waxy texture.

*Pubescence.*—Upper Surface: None. Lower Surface: None.

*Color of mature leaf.*—Upper Surface: RHS 143 A and RHS 142 C. Lower Surface: RHS 142 D, RHS 143 A.

*Color of immature leaf.*—Upper Surface: RHS 143 A and RHS 142 C. Lower Surface: RHS 142 D, RHS 143 A.

*Venation.*—Pattern: Longitudinal/parallel leaf shape. Color: None.

*Leaf fragrance.*—None.

Inflorescence description:

*Arrangement and type*.—Inflorescence.

*Orientation at opening*.—Out of the spile.

*Quantity*.—Per Plant with at least one open flower: About 60 at 2 weeks.

*Inflorescence size*.—Length: About 35 cm. Diameter: About 1.2 cm.

*Flower size*.—Length: About 6 cm. Diameter: About 0.5 cm. Depth: About 0.5 cm.

*Fragrance*.—None.

*Bud*.—

*Rate of opening*.—About 7 to 8 days, according to weather.

*Shape*.—Ovoid.

*Length*.—About 2 cm.

*Diameter*.—About 1 cm.

*Color*.—Apex: RHS 149 B. Base: RHS 142 B.

*Texture* (*both surfaces*).—Smooth.

Reproductive organs: (None observed).

*Androecium*.—Stamen: Number: 6 per flower. Length: About 1.2 mm. Color: RHS 150 D. Anther: Length: About 4 mm. Width: About 1 mm. Color: RHS 150 D. Filament: Length: About 1.3 mm. Color: RHS 150 D. Pollen: Amount: Moderate. Color: RHS 150 D.

*Gynoecium*.—Pistil: Number: One per flower. Length: About 1.5 mm. Stigma: Length: About 0.5 mm. Width: About 1 mm. Color: RHS 150 D. Style: Length: About 20 mm. Color: RHS 150 D. Ovary: Length: About 5 mm. Width: About 4 mm. Color: RHS 143 A.

Weather resistance: Drought Tolerant.

Disease/pest resistance: High resistance to antrachnose (*Colletotrichum sansevieriae*).

Disease/pest susceptibility: Not observed so far.

I claim:

1. A new and distinct *Sansevieria* plant named 'Graelyn', substantially as illustrated, and described herein.

* * * * *

A

B